United States Patent
Im et al.

(10) Patent No.: US 9,801,603 B2
(45) Date of Patent: Oct. 31, 2017

(54) METHOD AND APPARATUS FOR DETECTING DENTAL CARIES AND X-RAY IMAGING APPARATUS

(71) Applicants: VATECH Co., Ltd., Gyeonggi-do (KR); VATECH EWOO Holdings Co., Ltd., Gyeonggi-do (KR)

(72) Inventors: Se Yeol Im, Gyeonggi-do (KR); Dong Wan Seo, Gyeonggi-do (KR); Tae Hee Han, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 0 days.

(21) Appl. No.: 15/177,363

(22) Filed: Jun. 9, 2016

(65) Prior Publication Data
US 2016/0361037 A1 Dec. 15, 2016

(30) Foreign Application Priority Data
Jun. 9, 2015 (KR) ........................ 10-2015-0081296

(51) Int. Cl.
*A61B 6/00* (2006.01)
*A61B 6/14* (2006.01)

(52) U.S. Cl.
CPC ............ *A61B 6/5217* (2013.01); *A61B 6/145* (2013.01)

(58) Field of Classification Search
CPC ............ A61B 5/0088; G01N 21/6456; G01N 2021/1787; G06T 2207/30036; G06T 7/0012
See application file for complete search history.

(56) References Cited

U.S. PATENT DOCUMENTS

| | | | |
|---|---|---|---|
| 2007/0105069 A1* | 5/2007 | Yamagishi | A61B 5/0088 433/215 |
| 2009/0075228 A1* | 3/2009 | Kumada | A61B 5/0088 433/29 |
| 2012/0095732 A1* | 4/2012 | Fisker | A61C 13/0004 703/1 |
| 2012/0148986 A1* | 6/2012 | Yan | A61B 5/0088 433/215 |
| 2012/0328071 A1* | 12/2012 | Katsumata | A61B 6/14 378/4 |

* cited by examiner

*Primary Examiner* — Edward Park
(74) *Attorney, Agent, or Firm* — IP Legal Services, LLC

(57) ABSTRACT

The present invention relates to a method and apparatus for detecting dental caries and an X-ray imaging apparatus and, more particularly, a method and apparatus for detecting dental caries and an X-ray imaging apparatus that can automatically detect occurrence and the degree of progress of caries by processing dental X-ray images.

7 Claims, 4 Drawing Sheets

METHOD AND APPARATUS FOR DETECTING DENTAL CARIES AND X-RAY IMAGING APPARATUS

CROSS REFERENCE TO RELATED APPLICATION

The present application claims priority under 35 U.S.C. §119 to Korean Patent Application No. 10-2015-0081296, filed on Jun. 9, 2015.

BACKGROUND OF THE INVENTION

Field of the Invention

The present invention relates to a method and apparatus for detecting dental caries and an X-ray imaging apparatus and, more particularly, a method and apparatus for detecting dental caries and an X-ray imaging apparatus that can automatically detect occurrence and the degree of development of caries by processing dental X-ray images.

Description of the Related Art

Caries is a disease caused by breakdown of the hard tissues of teeth and bacteria are generally known as the cause.

In Korea, 80% of population have caries, and the development is clinically divided into four stages: The first stage of caries is limited to the enamel of a tooth; it develops to the dentine in the second stage; it develops to the nerve in the third stage; and in the fourth stage, there is only a remnant tooth root left with the crown breaking down.

In general, doctors detect caries by visually looking inside the mouth of a patient or checking dental X-ray images.

That is, according to the method of detecting caries in the related art, since doctors visually check the inside of the patient's mouth, it takes long time to determine caries and objective determination may not be made, so there may be an error in the determination.

Further, according to the method of detecting caries in the related art, doctors have to visually minutely check the inside of the patient's mouth even if the patient does not have caries, so there is difficulty in dental examination and treatment.

SUMMARY OF THE INVENTION

The present invention has been made in an effort to solve the problems and an object of the present invention is to provide a method and apparatus for detecting dental caries and an X-ray imaging apparatus that can automatically detect occurrence and the degree of development of caries by processing dental X-ray images.

Further, another object of the present invention is to provide a method and apparatus for detecting dental caries and an X-ray imaging apparatus that can automatically determine the degree of development of caries by detecting where caries occurs in a tooth.

Further, another object of the present invention is to provide a method and apparatus for detecting dental caries and an X-ray imaging apparatus that can reduce a diagnosis time by raising an alarm, when a patient has caries.

It should be noted that objects of the present invention are not limited to the above-mentioned object and other objects of the present invention will be apparent to those skilled in the art from the following descriptions.

In order to achieve the above object, according to one aspect of the present invention, there is provided a method of detecting dental caries that detects whether caries has occurred by processing a dental X-ray image, the method including: segmenting teeth in a dental X-ray image and determining whether dental caries has occurred using image values of the segmented teeth.

Further, according to another aspect of the present invention, there is provided an apparatus for detecting a dental caries in a dental X-ray image comprising: an input interface receiving image data of the dental X-ray image; a storage saving the image data and the dental X-ray image; and an image processor processing the dental X-ray image, segmenting the teeth and detecting the dental caries by image values of the teeth.

Further, according to another aspect of the present invention, there is provided an apparatus of detecting dental caries that includes an input interface, a display, a storage, and an image processor and detects whether dental caries has occurred by processing a dental X-ray image, in which the image processor segments teeth in a dental X-ray image and determines whether dental caries has occurred using image values of the teeth.

Further, according to another aspect of the present invention, there is provided an X-ray imaging apparatus including: an X-ray source radiating an X-ray to a patient's head including the patient's mouth; an X-ray sensor disposed opposite to the X-ray source and acquiring a dental X-ray image of the patient by receiving an X-ray passing through the patient's mouth; and an apparatus for detecting dental caries that segments teeth in the dental X-ray image and determines whether dental caries has occurred using image values of the segmented teeth.

Further, according to another aspect of the present invention, there is provided an intraoral X-ray imaging apparatus including: an X-ray source radiating an X-ray to the mouth of a patient; an intraoral sensor inserted into the mouth and acquiring a dental X-ray image of a structure inside the mouth; and an apparatus for detecting dental caries that segments teeth in the dental X-ray image and determines whether dental caries has occurred using image values of the segmented teeth.

The present invention has the following effects.

First, according to the method and apparatus for detecting dental caries and the X-ray imaging apparatus of the present invention, it is possible to automatically detect dental caries by processing a dental X-ray image, so it is possible to considerably reduce the time taken to detect caries and it is also possible to obtain an objective result in caries detection.

Further, according to the method and apparatus for detecting dental caries and the X-ray imaging apparatus of the present invention, by determining whether the dental caries occurs in enamel or dentine, it is possible to automatically determine the degree of development of caries in accordance with the position of caries.

Further, according to the method and apparatus for detecting dental caries and the X-ray imaging apparatus of the present invention, when caries has occurred, it is possible to reduce diagnosis time by raising an alarm and it is also possible to prevent unnecessary diagnosis by showing the degree of development of caries by outputting different sounds or images for an alarm.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION

Figure 1:
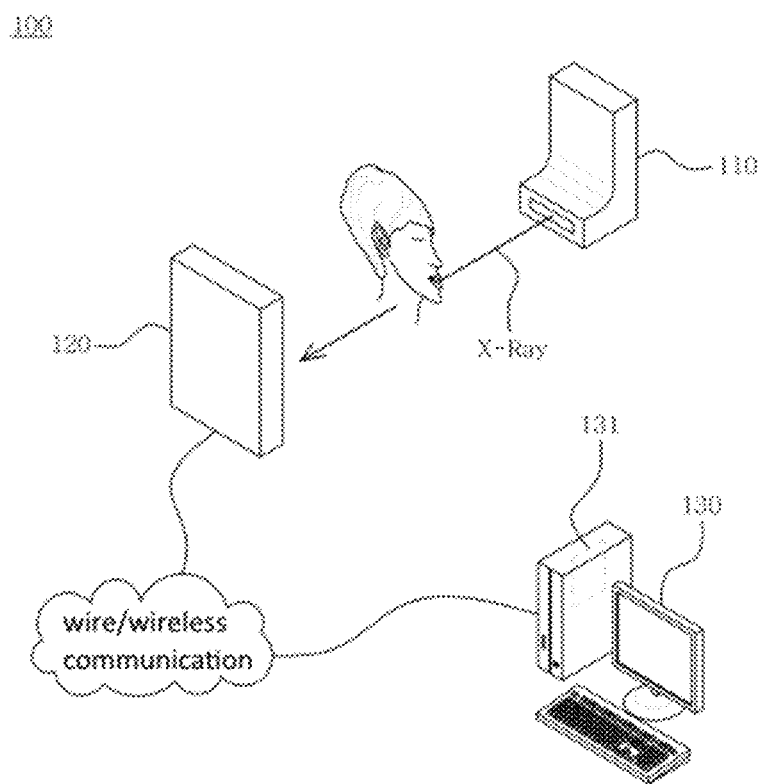
FIG. 1 is a view showing an X-ray imaging apparatus according to an embodiment of the present invention.

Terminologies used herein have been selected from that are extensively and generally used at present, but the applicant(s) has freely selected some terminologies in specific cases, so, in this case, the meanings should be understood not just from the names, but in consideration of the meanings stated or described in the following detailed description.

The technical configuration of the present invention is described hereafter in detail with reference to the embodiments shown in the accompanying drawings.

However, the present invention is not limited to the embodiments described herein and may be achieved in other ways. Like reference numerals indicate the same components throughout the specification.

Referring to FIG. 1, an X-ray imaging apparatus 100 according to an embodiment of the present invention includes an X-ray source 110 that radiates an X-ray to the head of a patient, an X-ray sensor that is disposed opposite to the X-ray source 110 and acquires a dental X-ray image from the X-ray passing through the head of a patient, and an dental caries detecting device 130 that detects dental caries of a patient by processing the dental X-ray image from the X-ray sensor 120.

Though not shown in the drawings, the X-ray imaging apparatus 100 according to an embodiment of the present invention may further include arms for supporting the X-ray source 110 and the X-ray sensor 120 and supports for supporting the arms on a floor or a wall.

Further, the arms may be rotary arms so that the X-ray source 110 and the X-ray sensor 120 can rotate around the head of a patient.

The dental caries detecting device 130, which may be a computer system connected with the X-ray sensor 120 through a wire or a wireless network and which can collect and process information, is, in a broad sense, an image processing system including other smart devices or an embedded system specifically manufactured for the X-ray imaging apparatus 100 of the present invention.

A dental caries detection program 131 for detecting dental caries 40 by processing the dental X-ray image may be embedded in the dental caries detecting device 130.

The dental caries detection program 131 may be provided in a recording medium independently from the X-ray imaging apparatus of the present invention, and the recording medium may be specifically designed for the present invention or may be common devices well known to those skilled in the art in the computer software field. For example, the recording medium may be a magnetic medium such as a hard disk, a floppy disk, and a magnetic tape; an optical recording medium such as a CD and a DVD; a magnetic-optical recording medium for both magnetic and optical recording; or hardware devices that can keep and execute program commands independently or in combination with each other such as a ROM, a RAM, and a flash memory.

The dental caries detection program 131 may be a program in which program commands, data files, and local data structure are configured independently or in combination with each other, or may be a program written by not only machine codes made by a compiler, but also high-class language codes that can be executed by a computer using an interpreter.

The present invention may further provide a server system that can keep the dental caries detection program 131 and can transmit the dental caries detection program 131 to a client system such as the dental caries detecting device 130 through a network.

That is, the dental caries detecting device 130 may download the dental caries detection program 131 from the server system and install it.

Figure 2:
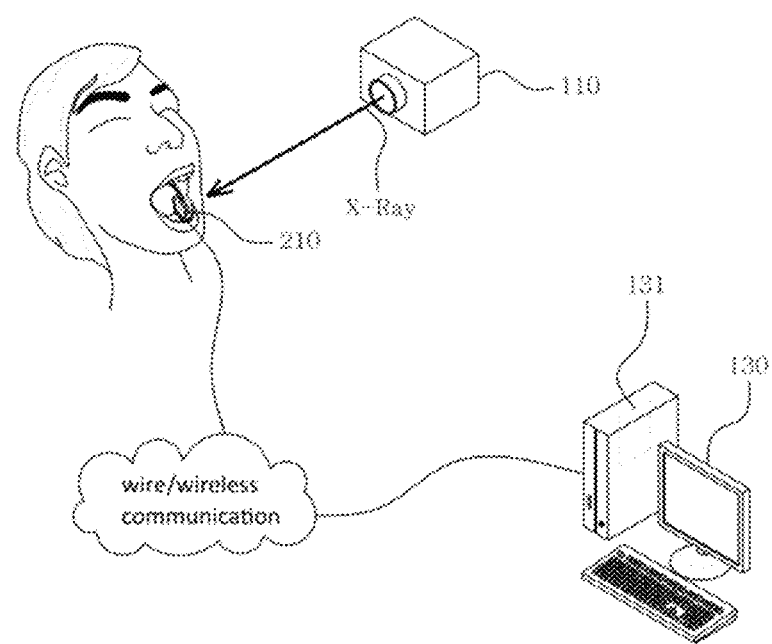
FIG. 2 is a view showing an intraoral X-ray imaging apparatus according to an embodiment of the present invention.

FIG. 2 shows an intraoral X-ray imaging apparatus 200 according to an embodiment of the present invention, in which, as compared with the X-ray imaging apparatus 100 shown in FIG. 1, the X-ray source 110 is substantially separated from an X-ray sensor such as a portable X-ray generator and the X-ray sensor 120 is replaced with an intraoral sensor 210 that is put into the patient's mouth to take X-ray images of the inside of the mouth, and the other components are substantially the same.

The X-ray source 110 may be directly carried by a worker or may be held on a wall etc. by an arm and the intraoral sensor 210 can acquire X-ray images of the intraoral structure between the X-ray source 110 and the intraoral sensor 210 by receiving X-rays from the X-ray source 110 outside the mouth.

The X-ray source 110 and the X-ray sensor 120 shown in FIG. 1 and the X-ray source 110 and the intraoral sensor 210 shown in FIG. 2 may be modified in various ways, depending on the types of dental X-ray images to be acquired.

For example, the X-ray source 110 and the X-ray sensor 120 shown in FIG. 1 may be used to take panoramic X-ray images, while the X-ray source 110 and the intraoral sensor 210 shown in FIG. 2 may be used to take X-ray images of teeth (two or three teeth) in a local area inside a mouth.

Figure 3:
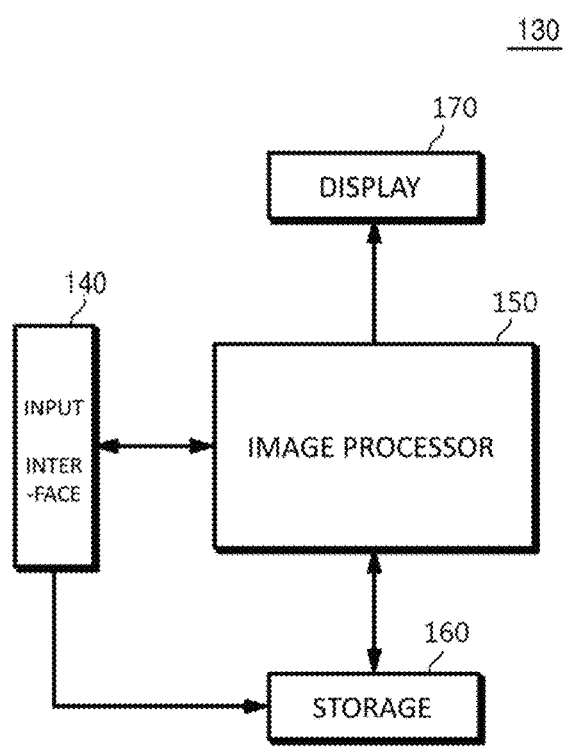
FIG. 3 is a block diagram of an apparatus for detecting dental caries according to an embodiment of the present invention.

FIG. 3 is a block diagram showing the dental caries detecting device 130 according to an embodiment of the present invention. As shown in FIG. 2, the dental caries detecting device 130 may include an input interface 140, an image processor 150, a storage 160, and a display 170.

The input interface 140 may be a hardware and software module for inputting user instructions for processing images according to various embodiments of the present invention. The input interface 140 may be advantageously used to input various necessary instructions to the image processor 150, input X-ray image data from the X-ray sensor 120 to the storage 160, or indicate some or all of X-ray images displayed by the display 170 so that the images can be processed. For example, the input interface 140 may include a keyboard, a keypad, a touch pad, and a mouse for a computer, but is not limited thereto. For example, the input interface 140 may also include a graphic user interface that can be controlled using the input devices described above.

The display 170, which is provided to display images obtained in accordance with various embodiments of the present invention, may include various display devices such as an LCD display, an LED display, an AMOLED display, and a CRT display.

The storage 160 may be used to keep X-ray images. The storage 160 may be used to keep image data obtained from a medium result in the process of processing images according to various embodiments of the present invention, resultant image data obtained by processing images according to various embodiments of the present invention, and variables required for processing images according to various embodiments of the present invention. In various embodiments, the storage 160 may keep various types of images described above in a DICOM (Digital Image Communications in Medicine) format or common image formats (BMP, JPEG, and TIFF etc.). The storage 160 may further keep software and firmware for configuring the image processor 150. The storage 160 may be any one recording medium of a flash memory type, a hard disk type, an MMC (MultiMedia Card), a card type memory (for example, an SD (Secure Digital) card or an XD (eXtream Digital) card), a RAM (Random Access Memory), an SRAM (Static Random Access Memory), a ROM (Read-Only Memory), an EEPROM (Electrically Erasable Programmable Read-Only Memory), a PROM (Programmable Read-Only Memory), a magnetic memory, a magnetic disk, and an optical disk, but those skilled in the art may understand that the storage 160 is not limited to these devices.

The image processor 150 can detect dental caries 40 by reading out some of or the entire X-ray image data from the storage 160, and for this purpose, the image processor 150 can segment teeth in an X-ray image and determine whether dental caries 40 occurs in the teeth using at least one image value selected from contrast and brightness of the teeth. In the embodiments, the brightness is selected as the image value.

In particular, when an X-ray image is a panoramic X-ray image of an upper dentition 11 and a lower dentition 12, the image processor 150 can detect the occlusal surface 13 between the upper dentition 11 and the lower dentition 12 and segment the teeth using normal vectors perpendicular to the occlusal surface 13. Further, the image processor 150 can segment enamel 31 and dentine 32 of the segmented teeth and can determine whether the dental caries 40 occurs in the enamel 31 or the dentine 32 by image values of enamel 31 and dentine 32. Further, with the information of the part where the dental caries occurs, the image processor 150 can determine the degree of development of dental caries, and when the image processor 150 determines that dental caries 40 has occurred, it can raise an alarm saying that dental caries 40 has occurred through a voice, a text or an image. To this end, the dental caries detecting device 130 according to an embodiment of the present invention may include a speaker for outputting a voice or a sound, or a display unit for outputting the text or the image.

The image processor 150 may be achieved by using at least one of an ASIC (Application Specific Integrated Circuit), a DSPD (Digital Signal Processors DSP), a DSPD (Digital Signal Processing Device), a PLD (Programmable Logic Device), an FPGA (Field-Programmable Gate Array), a processor, a controller, a microcontroller, and a microprocessor. Further, the image processor 150 may be a firmware/software module that can be executed on the hardware platforms described above. In this case, the firmware/software module may be configured by one or more software applications written by an appropriate program language.

A method of detecting dental caries 40 according to an embodiment of the present invention is described hereafter with reference to FIGS. 1 to 4.

Figure 4:
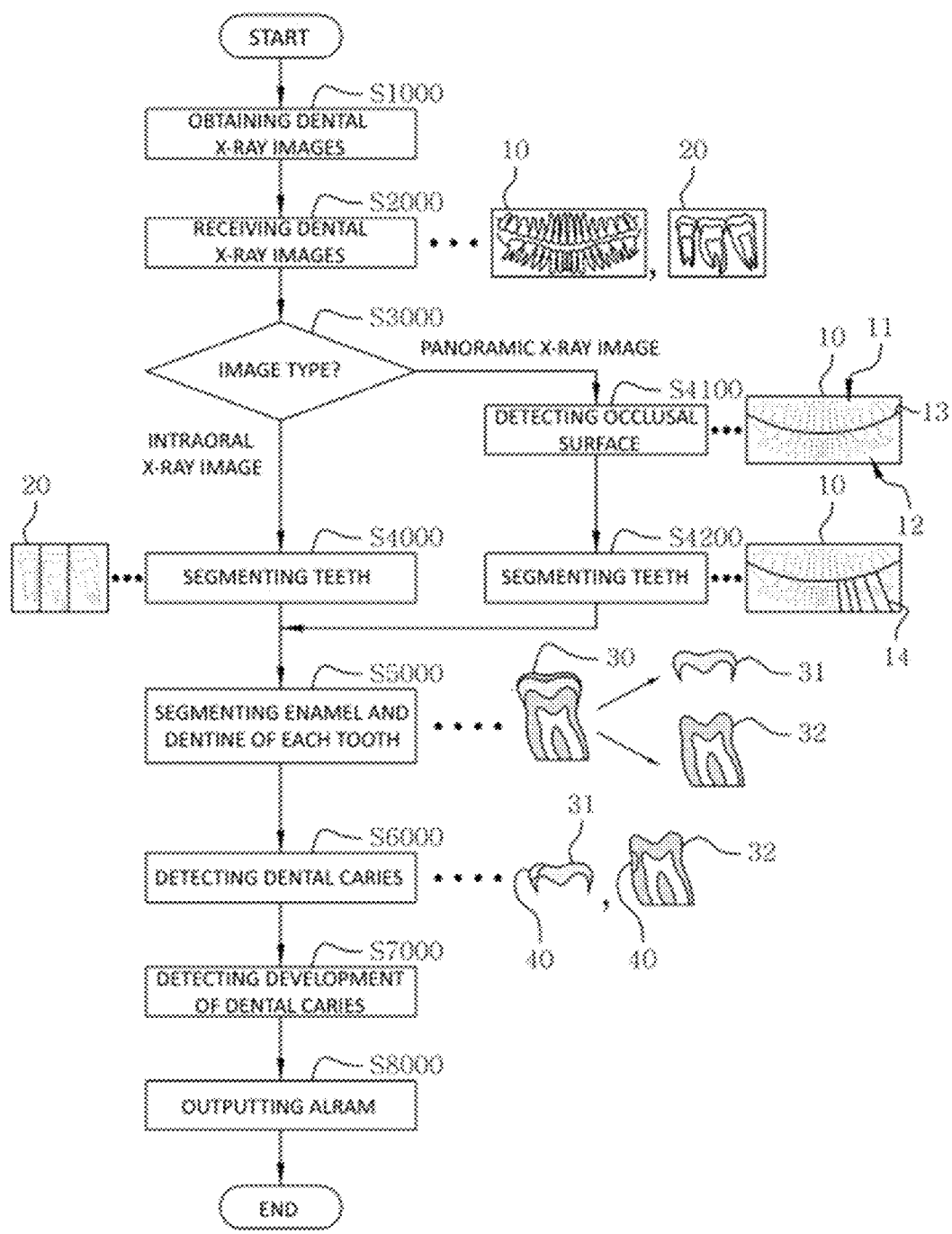
FIG. 4 is a flowchart of a method of detecting dental caries according to an embodiment of the present invention.

Referring to FIG. 4, the method of detecting dental caries 40 of the present invention is started from the X-ray imaging apparatus 100 or the intraoral X-ray imaging apparatus 200 according to embodiments of the present invention.

First, dental X-ray images of a patient are obtained by the X-ray sensor 120 or the intraoral sensor 210 (S1000), and the dental caries detecting device 130 receives the dental X-ray images 10 and 20 (S2000).

Further, the dental X-ray images that the dental caries detecting device 130 receives may be a panoramic X-ray image 10 or an intraoral X-ray image 20 and may be kept in the storage 160.

Next, the image processor 150 segments the teeth in the dental X-ray images.

In order to segment the teeth in the dental X-ray images, a detection algorithm that uses contrast differences between the pixels in dental X-ray image data may be used.

In order to segment the teeth in the dental X-ray images, a binarization algorithm which implements a thresholding method or a histogram-based method can be used. The thresholding method check a brightness of each pixel or representative brightness of adjacent pixels of an X-ray image by a threshold value T to give a white value (brightness=1) for values larger than T and a black (brightness=0) for values smaller than T. The histogram-based method (or an Otsu's method) makes a histogram on the basis of brightness of pixels in an X-ray image and finds a threshold value that can divide the histogram into two groups. The threshold value can be an optimum threshold value such that a distribution of the histogram in each group may be minimized and a distribution of the histogram between the groups may be maximized.

Alternatively, in order to segment the teeth in the X-ray images, an SRG (Seeded Region Growing) algorithm can be implemented. With the SRG (Seeded Region Growing) method a seed which is a position of an area to be expanded in an X-ray image can be designated and an area can be expanded from the seed by comparing brightness using a predetermined reference. If a difference between a peripheral pixel and the seed pixel is below the predetermined reference, the area can be expanded. Or if the difference between the peripheral pixel and the seed pixel exceeds the predetermined reference, the expansion of the area can be stopped. For the expansion direction of the area, 4-connectivity for moving up, down, left, and right or 8-connectivity for moving the directions of 4-connectivity and diagonal directions of them may be used.

Further, in order to segment the teeth in the X-ray images, a level-set technique may be used. With the level-set algorithm a curve can be advanced by iterating updates an initial contour of the curve and a contour converges to a boundary of a subject.

Further, in order to segment the teeth in the X-ray images, an edge detection algorithm may be used. With the edge detection technique, a contour can be extracted by applying a Sobel-Mask, a Prewitt mask, a Robert mask, a canny mask, and a Laplacian mask to a dental X-ray image.

On the other hand, when the dental X-ray image is the oral X-ray image 20, there are two to three teeth in the image. So it is not that difficult to segment the teeth using a detection algorithm like the contrast of an X-ray image. But when the dental X-ray image is the panoramic X-ray image 10, because all of the teeth of the upper dentition 11 and the lower dentition 12 are included in the image, it is difficult to segment the teeth.

In the case that the dental X-ray image is the panoramic X-ray image 10, the image processor 150 detects the occlusal surface 13 of the upper dentition 11 and the lower dentition 12 using a detection algorithm implementing differences in contrast (S4100), and then segments the teeth in the upper dentition 11 and the lower dentition 12 using a boundary detection algorithm and normal vectors perpendicular to the occlusal surface 13 (S4200). In this case, it is possible to considerably reduce the amount of calculation, so that the segmentation of the teeth can be done in real time.

Further, though not shown in the drawings, a process of assigning an identifier to the segmented teeth may be performed. This is for a doctor to easily recognize where a segmented tooth should be placed.

Next, the image processor 150 segments enamel 31 and dentine 32 in the segmented teeth 30 (S5000).

The detection algorithm and the image segmentation method using a difference in contrast of enamel 31 and dentine may be used to segment the enamel 31 and the dentine 32 without a limit.

Next, the image processor 150 detects a dental caries 40 in the segmented enamel 31 and dentine 32 and then determines whether caries occurs.

Further, in an image by the image processor 150, a dental caries portion is darker than normal portions. So the image processor 150 can determine whether caries occurs using an image value (a brightness value) of a tooth. For example, when the average brightness of the enamel 31 or the dentine 32 is less than threshold brightness, or when the average brightness of one or more of sections which are divided from the enamel 31 or the dentine 32 is less than the threshold brightness, to the image processor 150 may determine that the dental caries 40 has occurred.

Further, if the enamel 31 or the dentine 32 is divided into a plurality of sections and then the image processor 150 can find out where the dental caries 40 occurs.

That is, a doctor can easily and quickly find out whether dental caries 40 occurs even though he or she cannot see the dental caries 40 directly.

Next, the image processor 150 can further determine the degree of development at each portion where dental caries 40 has occurred (S7000).

For example, when dental caries 40 is detected only at the enamel 31, the first stage of caries may be determined, and when the dental caries 40 is detected at both of the enamel 31 and the dentine 32, the second stage of caries may be determined.

Further, if the dental caries 40 is not detected at the enamel 31 but only detected at the dentine 32, it can be determined that dental caries 40 has occurred at the lower portion of a tooth where the enamel 31 does not exist.

Further, although it is exemplified to detect dental caries 40 at the enamel 31 and the dentine 32 in the present invention, it may be possible to further detect dental caries 40 in the nerve or the crown of a tooth, and in this case, it is possible to minutely divide and determine the dental caries 40.

Next, when it is determined that there is a dental caries 40, the image processor 150 outputs the fact that the dental caries has occurred by a voice or an image for a doctor to recognize the fact (S8000).

To this end, the dental caries detecting device 130 of the present invention may further include a speaker other than the display 170. Further, the alarm saying that dental caries 40 has occurred may be raised with different voices or images in accordance with the degree of development of dental caries 40. It is possible to discriminate the degree of development of dental caries 40 by giving different melodies or volumes for the voice and giving different letters, colors, characters, symbols, and emoticons for the image.

Accordingly, a doctor can simply and quickly recognize not only whether dental caries 40 has occurred, but also whether dental caries 40 is developed.

Although preferable embodiments of the present invention were described above with reference to the drawings, they are not limited thereto and may be changed and modified by those skilled in the art without departing from the scope of the present invention.

What is claimed is:

1. An apparatus for detecting a dental caries in a dental X-ray image comprising:
  an input interface configured to receive image data of the dental X-ray image;
  a memory configured to store the image data and the dental X-ray image; and
  an image processor configured to process the dental X-ray image, segmenting the teeth and detecting the dental caries by image values of the teeth,
  wherein the image processor is configured to segment the teeth by an occlusal surface of an upper dentition and a lower dentition by detecting the occlusal surface between the upper dentition and the lower dentition and segmenting the teeth of the upper dentition and the lower dentition using normal vectors perpendicular to the detected occlusal surface, wherein the image processor is further configured to segment an enamel and dentine of each tooth in the panoramic dental X-ray image, and detect whether the dental caries has occurred by determining whether an average brightness of the enamel and dentine is less than a threshold brightness.

2. The apparatus of claim 1, wherein the image processor is configured to further provide a dental caries information.

3. An X-ray imaging apparatus comprising:
  an X-ray source configured to radiate an X-ray to a patient's head including the patient's mouth;
  an X-ray sensor disposed opposite to the X-ray source and configured to acquire a dental X-ray image of the patient by receiving an X-ray passing through the patient's mouth; and
  an apparatus configured to detect dental caries that segments teeth in the dental X-ray image and determines whether dental caries has occurred using image values of the segmented teeth,
  wherein the apparatus is configured to segment the teeth by detecting an occlusal surface between an upper dentition and a lower dentition and segmenting the teeth of the upper dentition and the lower dentition using normal vectors perpendicular to the detected occlusal surface, wherein the apparatus is further configured to segment an enamel and dentine of each tooth in the panoramic dental X-ray image, and detect whether the dental caries has occurred by determining whether an average brightness of the enamel and dentine is less than a threshold brightness.

4. A method of detecting dental caries by processing a dental X-ray image, the method comprising:
  taking a panoramic dental X-ray image of an upper dentition and a lower dentition;
  detecting an occlusal surface between the upper dentition and the lower dentition;
  segmenting the upper dentition and the lower dentition using normal vectors perpendicular to the detected occlusal surface in the panoramic dental X-ray image;
  segmenting an enamel and dentine of each tooth in the panoramic dental X-ray image; and
  detecting whether the dental caries has occurred by determining an average brightness of one of the enamel and dentine is less than a threshold brightness.

5. The method of claim 4,
  wherein the determining of whether the dental caries has occurred includes a process of determining whether the dental caries has occurred in the enamel or the dentine using image values of the enamel and the dentine.

6. The method of claim 5, further comprising determining the degree of development of the dental caries, depending on whether the dental caries has occurred in the enamel or the dentine, after the determining of whether the dental caries has occurred.

7. The method of claim 4, further comprising outputting a fact that the dental caries has occurred through a voice, a text or an image when determining that the dental caries has occurred, after the determining of whether the dental caries has occurred.

* * * * *